United States Patent [19]
Cecchetti et al.

[11] Patent Number: 5,509,917
[45] Date of Patent: Apr. 23, 1996

[54] LENSED CAPS FOR RADIAL MEDICAL LASER DELIVERY DEVICES

[75] Inventors: Walter Cecchetti, Padova; Stefano Guazzieri, Venice, both of Italy

[73] Assignee: CeramOptec Industries, Inc., East Longmeadow, Mass.

[21] Appl. No.: 265,058

[22] Filed: Jun. 28, 1994

[51] Int. Cl.⁶ ......................................... A61B 17/36
[52] U.S. Cl. ..................... 606/15; 606/13; 606/14; 606/17
[58] Field of Search ..................... 606/7, 13–18; 128/4, 6; 607/88, 89

[56] References Cited

U.S. PATENT DOCUMENTS

| | | | |
|---|---|---|---|
| 4,669,467 | 6/1987 | Willett et al. | 606/7 |
| 4,740,047 | 4/1988 | Abe et al. | 128/4 X |
| 4,778,247 | 10/1988 | Carpenter | 128/4 X |
| 4,787,370 | 11/1988 | Kanamori | 128/6 |
| 4,832,024 | 5/1989 | Boussignac et al. | 606/15 |
| 4,842,350 | 6/1989 | Sottini et al. | 606/7 X |
| 5,061,265 | 10/1991 | Abela et al. | 606/7 |
| 5,163,935 | 11/1992 | Black et al. | 606/7 X |
| 5,167,686 | 12/1992 | Wong | 606/7 |
| 5,292,320 | 3/1994 | Brown et al. | |
| 5,342,355 | 8/1994 | Long | 606/15 X |

FOREIGN PATENT DOCUMENTS 778276  7/1957  United Kingdom ................ 128/4

OTHER PUBLICATIONS

Costello, Anthony J.; Douglas E. Johnson; Damien M. Bolton, "Nd: YAG Laser Ablation of the Prostate as a Treatment for Benign Prostatic Hypertrophy", *Lasers in Surgery and Medicine* 1992; 12:121–124.

*Primary Examiner*—Stephen C. Pellegrino
*Assistant Examiner*—Michael Peffley
*Attorney, Agent, or Firm*—Bolesh J. Skutnik

[57] ABSTRACT

The device of the present invention pertains to a modified medical laser delivery device with sideways directed radiation that can produce high power densities at a distance further away from the fiber, thereby enabling non-contact ablating procedures to be carried out with lower laser input power levels.

8 Claims, 3 Drawing Sheets

LENSED CAPS FOR RADIAL MEDICAL LASER DELIVERY DEVICES

BACKGROUND OF THE INVENTION

1. Field of the Invention

The present invention is directed to the use of optical fibers capable of transmitting high density laser energy to internal body sites in microsurgery applications, thereby providing minimally invasive surgical techniques. The types of fibers used in these applications are referred to as side firing fibers, or simply side fibers, because they transmit the laser energy approximately perpendicular to the longitudinal axis of the optical fiber. The method of visual laser ablation prostatectomy (VLAP) has common application in the ablation of tissue in benign prostate hypertrophy (BPH).

2. Statement of Prior Art

Several attempts have been made at using laser therapy in the art of BPH. The following represents the state of the art:

In the article entitled, "Nd:YAG Laser Ablation of the Prostate as a Treatment for Benign Prostatic Hypertrophy", Costello, et al disclose a quartz fiber used to deliver laser energy via a gold-plated metal alloy tip containing a hollow deflecting device.

U.S. Pat. No. 5,292,320 to Brown et al. discloses a device capable of delivering high laser power at selected angles to the axis of the optical fiber.

Notwithstanding, the prior art which teaches numerous variations on the idea of the use of optical fibers in the art of laser ablation of tissue, none of the prior art teaches the system of the present invention involving a medical delivery optical fiber in which the distal tips have been modified to yield sideways directed radiation with high power densities at further distances from the fiber. This configuration enables non-contact ablation procedures to be accomplished with lower input laser power levels, and permits simpler, more compact and more economical laser sources to be employed.

SUMMARY OF THE INVENTION

The present invention pertains to a modified medical laser delivery device with sideways directed radiation that can produce high power densities at a distance further away from the fiber, and thus enable non-contact ablating procedures to be carried out with lower laser input power levels. Another aspect of the present invention involves an innovative manufacturing method to accomplish this goal. Yet another aspect of this invention describes a novel design and method to affix caps to the optical fibers in a permanent manner unaffected by thermal heating of the device in operation. A further aspect of this invention involves the reduction of Fresnel reflections.

These aspects of the present invention can be achieved in several manners. These include shaping part of a transparent quartz glass cap into a lens in the main exit direction of the beam; using highly refractive optical materials, such as transparent sapphire, as the cap, and shaping a portion thereof into a lens in the main exit direction; or, more generally, using caps made of any medically suitable material and inserting a microlens in the exit path of the beam. The glass cap can be fused with the fiber at the point of the main beam exit thus effectively reducing Fresnel losses. The glass cap can be further fused with the fiber around the entire circumference to permanently seal it onto the fiber tip. This fusion is possible by utilizing a new innovative laser heating and fusing mechanism. When this fusion is performed, before the lens is formed, in the region of the beam path (sideways directed), the formation of a focusing lens is greatly simplified. The present invention and its modifications will be more clearly understood when taken in conjunction with the following drawings.

BRIEF DESCRIPTION OF THE DRAWINGS

The present invention is more fully understood when the instant specification is taken in conjunction with the drawings which are appended hereto, wherein:

FIG. 2b shows an end view of the fiber of FIG. 2a;

FIG. 3b shows an end view of the fiber of FIG. 3a;

FIG. 4b shows an end view of the fiber of FIG. 4a;

FIG. 5b shows an end view of the fiber of FIG. 5a;

FIG. 6b shows an end view of the fiber of FIG. 6a.

DETAILED DESCRIPTION OF THE INVENTION

The present invention involves a modified medical laser delivery device with sideways directed radiation that can produce high power densities at a distance further away from the fiber and thus enable non-contact ablating procedures to be carried out with lower laser input power levels.

Figure 1:
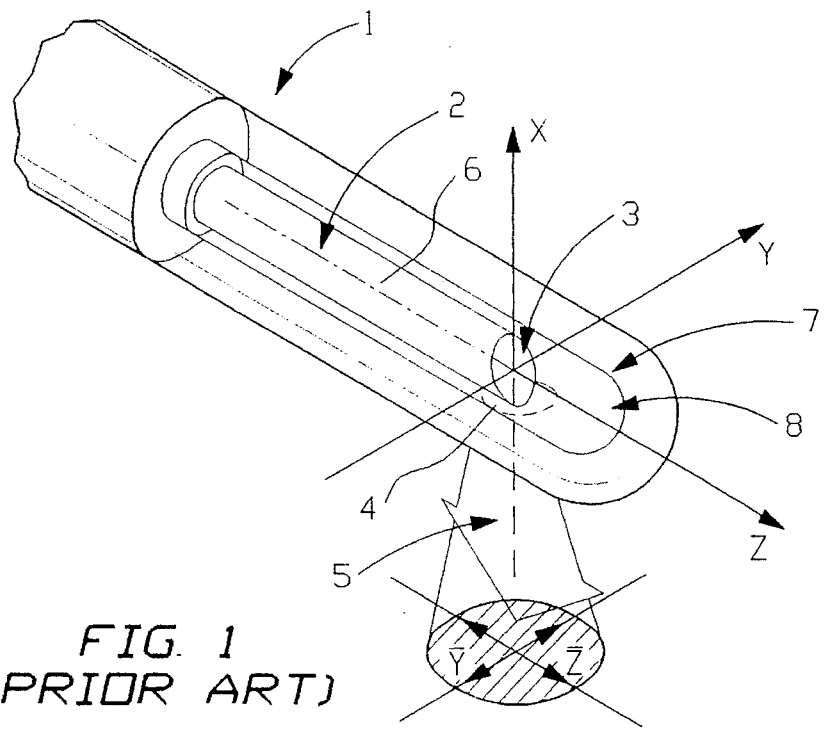
FIG. 1 shows a plane view of a basic prior art medical laser delivery system of the refractive type with an obliquely cut tip.

FIG. 1 shows a present state of the art laser delivery system 1 of the refractive type. The laser beam 5 in the optical fiber 2 is totally reflected down toward the side 4 of the fiber 2 using an obliquely cut tip 3 due to the refractive index differences between the fiber core 6 and that of the air gap 8 formed in the cap 7. As depicted in the figure, the sideways irradiated beam 5 diverges in the YZ plane as it leaves the fiber 2 and passes through the transparent quartz cap 7 into the body fluids of the patient. In operation, the device 1 removes unwanted tissue by a photothermic effect arising from the absorption of the laser energy by the tissue. This effect on the tissue induced by laser radiation is strongly dependent on the power density of the laser energy at the tissue surface. If the spot size increases by merely 20%, for example, the laser power exiting the fiber must be 45% greater to provide the same power density. The limitations of the present art and the problems which arise in its application are thus illustrated.

Figure 2A:
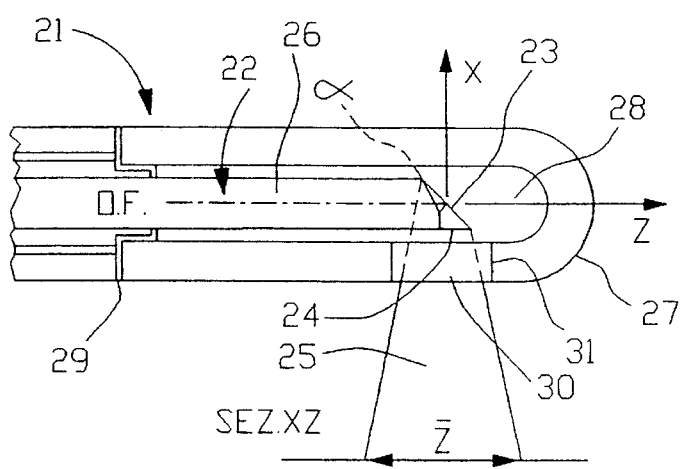
FIG. 2a shows a cross-section of the side fiber of the device of the present invention.
Figure 2B:
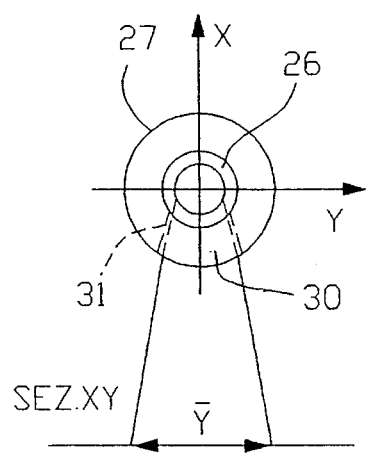

One embodiment of the present invention, as depicted in FIGS. 2a and 2b, includes the features as described in FIG. 1, in addition to other elements as herein described. Thus, the device 21 of the present invention includes an optical fiber 22 comprising a core 26 with an oblique cut tip 23, and a cap 27 attached to the fiber 22 using glue 29 or other such substances, with an air gap 28 being formed between the fiber 22 and the cap 27. As with the device 1 of the prior art, the device of the present invention reflects a laser beam 25 out the side 24 of the fiber 22. However, in the case of the present invention, the cap 27 includes a sector 30 having an optical part which intersects the exiting laser beam as demarcated by a profile region 31. This unique design allows sideways directed radiation that can produce high power densities at a distance further away from the fiber by focusing the exiting laser beam.

Figure 3A:
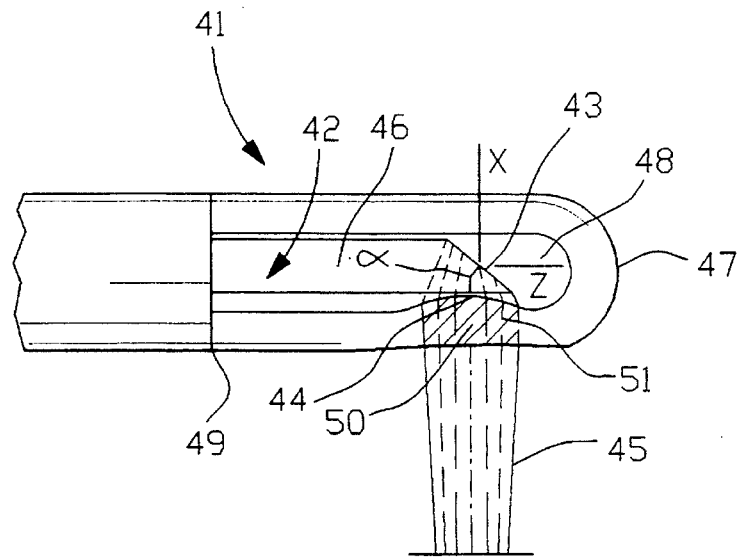
FIG. 3a shows a cross-section of the side fiber of the present invention with a lens formed in the quartz cap.
Figure 3B:
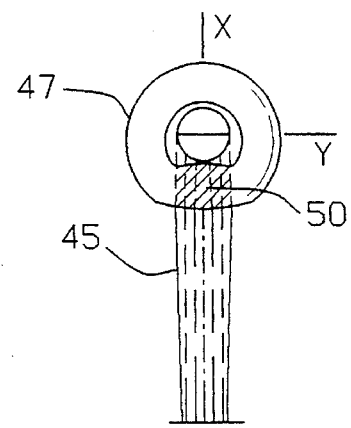

Other embodiments, the preferred embodiments, are shown with a lens placed in the cap including that of FIGS. 3a and 3b. The construction and operation of this embodiment is described in the following example, whereby an optical fiber 42 manufactured by CeramOptec, type Optran UV 600/660, was used. The fiber 42 consisted of a 600 micrometer diameter pure silica core 46 with a 660 micrometer O.D. fluorinated silica cladding, with a numerical aperture of 0.22. The fiber tip 43 was exposed and cut with a prismatic angle of alpha= 40 degrees to obtain the total side deflection of the radiation 45. A transparent quartz or pure silica cap 47 of I.D. 900 micrometers and O.D. 1800 micrometers was used to provide an air gap 48 guaranteeing the change of refractive index to be greater than 1.6 and to protect the mechanical integrity of the tip 43. A 25 W CO2 laser was coupled with a plano-convex lens of 25 cm focal length to fuse the transparent quartz cap 47 to create the internal curvature 50 shown in FIGS. 3a and 3b. The quartz cap 47 was glued to the fiber 46 at a point 49. The radiation 45, reflected from the cut tip 43 intersects and passes through the sector 50 of the quartz lens cap 51.

The central rays and low divergent rays from the fiber core center were focused by the cap lens 51. The external surface had little or no additional effect on the optics since it is basically in a water medium; and the refractive indices of water and quartz are very similar. By fusing the transparent quartz glass 47 in the sector 50 into the correct profile, the lens 51 formed can collimate the output beam 45 and make the power density remain essentially unchanged as the probe 41 is moved further away from the tissue surface to be treated.

Figure 4A:
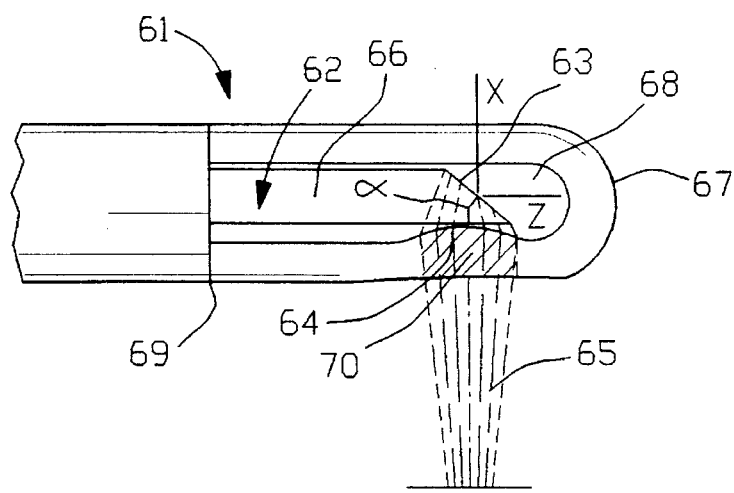
FIG. 4a shows a cross-section of the side fiber with a lens formed in the cap made of a highly refractive material.
Figure 4B:
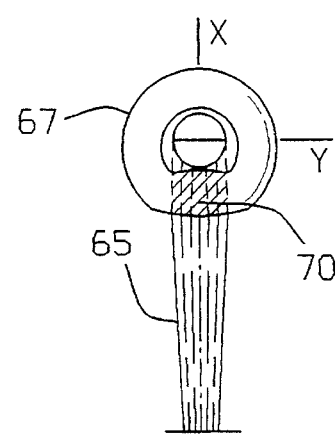

FIGS. 4a and 4b depict another embodiment of the present invention using a fiber 62 similar to that in FIG. 3a and 3b and replacing the transparent quartz cap 47 with a cap made of transparent sapphire 67 with essentially the same dimensions as the quartz cap 47. A lens 64 is created in the area of the sector 70 using a CO2 laser similarly as in the previous example within the sapphire cap 67. The sapphire cap 67 is glued to the fiber 62 at a point 69. The cap 67 guarantees both the change in index of the fiber core 66 to air interface necessary for the lateral re-direction of the beam 65 (sideways) and the optical and mechanical integrity of the fiber tip 63. The output radiation 65 intersects with the sector 70 of the sapphire lens cap 64, 67.

Measurements taken at the distal tip 63, as before, determined similar results to those obtained with the quartz lens cap 47, 51, but due to the much higher refractive index of sapphire, an external focusing effect occurred as the beam exited into the water (body fluid) which permitted greater focusing power than for an equivalent lens profile 51 in the quartz cap 47. This feature permits the use of simpler geometrical profiles for the sapphire lens cap 64 than for the transparent quartz lens cap 47, 51. Additionally, at higher temperature, stability of the sapphire together with the possibility of placing the focal point closer to the cap surface can provide very high power densities near the surface of the capped fiber for highly efficient removal of the prostate tissue.

Figure 5A:
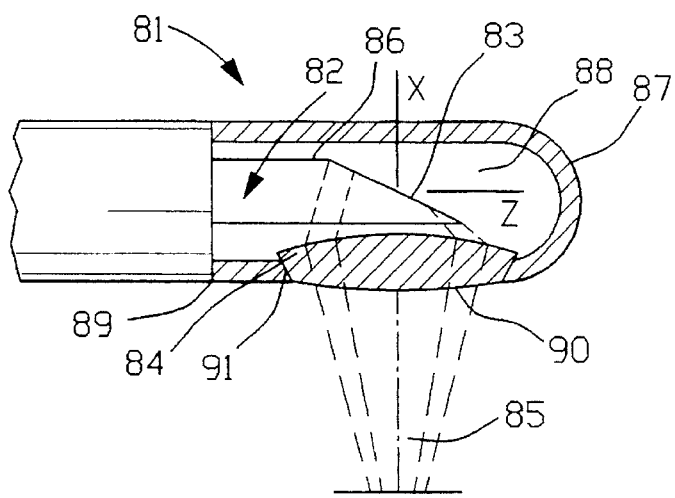
FIG. 5a shows a cross-section of the side fiber with a cap made of a material suitable for obtaining focused or collimated laser radiation output.
Figure 5B:
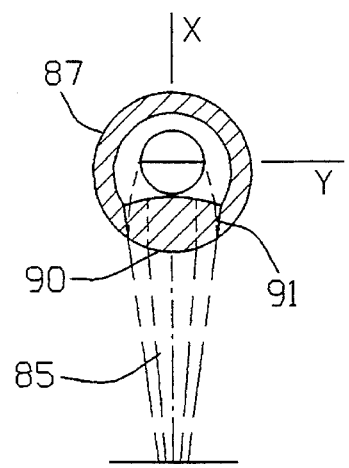
Figure 6A:
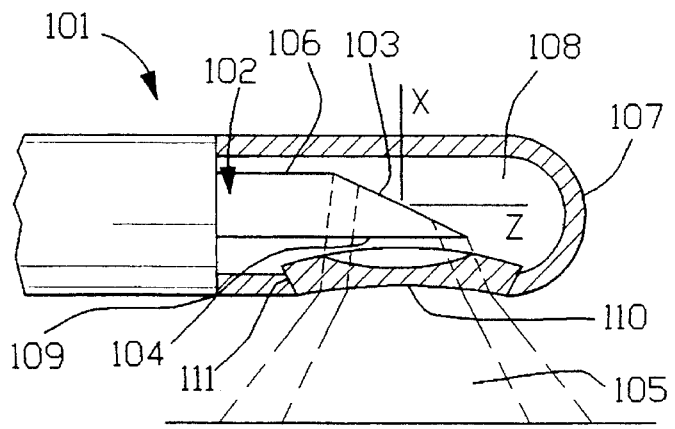
FIG. 6a shows a cross-section of the side fiber with a cap made of a material suitable for obtaining selectively divergent laser radiation output.

Other preferred embodiments of the invention are revealed in FIGS. 5a–5b and 6a–6b. In addition to full sapphire caps 67, metals and other materials have also been used as cap material. A sapphire microlens 90, 110, as shown in FIGS. 5a and 6a respectively, has been inserted into an opening or profile 91, 111 of the sector in each cap 87, 107. The profile 91, 111 may be conical to prevent the possibility of the microlens 90, 110 from falling out during treatment. However, the shape of the opening can vary with adjustments to the microlens.

More specifically, as shown in FIGS. 5a and 5b, the device described above includes an optical fiber 82 comprising a core 86 with an oblique cut tip 83, and a cap 87 made from gold, or any such material, attached to the fiber 82 using a glue material 89, with an air gap 88 being formed between the fiber 82 and the cap 87. The cap 87, as previously described herein, contains a transparent sapphire microlens 90 for bi-directional focusing.

Figure 6B:
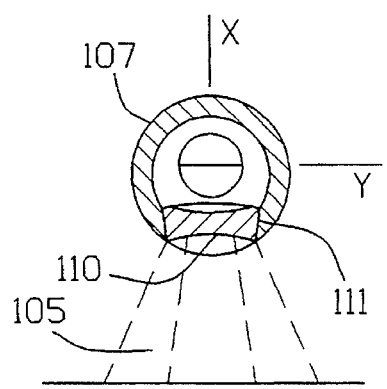

FIGS. 6a and 6b show a device as described above including an optical fiber 102 comprising a core 106 with an oblique cut tip 103, and a cap 107 made from gold attached to the fiber 102 using a glue material 109, with an air gap 108 being formed between the fiber 102 and the cap 107.

One advantage of this embodiment of the present invention is the fact that the lenses can be fabricated with very specific focal strengths and optical characteristics. It is even possible to make ones with specific diffusing characteristics which would be advantageous for photodynamic therapy of tumors. These diffusing characteristics are attributed to the unique structures as described above, including means for collimating and focusing the output beam and lens' having conical profiles.

Another aspect of the present invention involves a method for manufacturing the device of the present invention. The plastic protective coatings are typically removed to expose 10 to 20 mm of the fiber end, with the exposed end then being polished to the desired oblique angle, e.g. 40 degrees, as shown in the figures. The fiber is held in a small lathe chuck by the plastic coating near the stripped section, while the quartz cap or other such cap as herein described is held in another chuck on the lathe. The cap is placed over the exposed fiber by bringing the chucks toward eachother. Setting both chucks into synchronous rotating motion, a CO2 laser beam is directed at the cap in a sufficiently diffuse manner so as to heat the cap to a temperature of approximately 300 degrees C. The temperature can be regulated and held constant by sensing the cap's temperature via suitable IR sensors and controlling the laser output accordingly. A second CO2 laser beam with approximately 10 W of power is then directed onto the cap near its open end, and the cap is bonded to the fiber (circumferentially fused to the fiber), providing a much more thermally stable junction to the fiber than the gluing approach normally employed. The spinning lathe is stopped and the diffuse radiation is discontinued. The cap, with the hot gas it contains, is allowed to cool, creating a gas pocket, then the 10 W CO2 laser is directed to the sector of the cap where the sideways deflected beam will emerge from the assembly. The glass in the sector softens and collapses toward the fiber, simultaneously spot fusing to the fiber and forming a converging lens equivalent to that shown in FIG. 3. In this manner, the cap is modified at the sector. This optical shape achieves multiple goals: the high intensity low order modes at the center of the fiber core can pass through the device without Fresnel reflections, while the higher order modes further away from the core axis are focussed by the lens produced by this process. Thus, instruments such as diode lasers, which tend to have a large divergence from their output end, are more efficiently focussed by the device/lens of the present invention. In addition, the slightly collapsed outer cap surface resulting from this manufacturing process creates no optical problems due to the closeness of the refractive indices of quartz, and other such materials, and the water surrounding the cap in operation. Thus, the prismatic cut fiber and bi-directional lens allow for total reflection, and provide for rays to pass without Fresnel losses, respectively.

The above disclosed method could be modified such that after a prismatic tip is cut on a distal end of the fiber, the end is covered by a protective cap that is prepared such that an opening is formed in a sector of the cap. The opening is used to position and retain a microlens that can focus, collimate or precisely diverge an output beam as it passes through the sector during operation, and may be formed by machining processes. The protective cap is then bonded to the fiber to create a gas pocket around the prismatic fiber tip, in a manner described above.

In operation, the optical fiber is connected to a medical laser source at its proximal end such that the distal end directs an output beam in a desired fashion.

Obviously numerous modifications and variations of the present invention are possible in light of the above teachings. It is therefore understood that within the scope of the appended claims, the invention may be practiced otherwise than as specifically described herein.

What is claimed is:

1. A medical laser delivery device comprising:

an optical fiber terminated at a proximal end so that it can be connected to a medical laser source, and with a distal end having a prismatic cut fiber tip for sideways directing of an output beam by total reflection;

said fiber's distal end enclosed by a cap whose open end is bonded to said fiber so as to create a gas pocket around said prismatic cut fiber tip; and a sector of said cap, lying within said output beam direction, being converted, after said cap is bonded to said fiber, into a bi-directional lens for focusing said output beam as it exits said device into a surrounding medium.

2. A medical laser delivery device according to claim 1, wherein said focusing said output beam includes collimating said output beam by means of said bi-directional lens.

3. A medical laser delivery device according to claim 1, wherein said bi-directional lens is fused to said fiber in a central area of said lens to provide scatter free transmission of said output beam.

4. A medical laser delivery device according to claim 1, wherein said cap is bonded at its open end to said fiber by being circumferentially fused to said fiber.

5. A method of manufacturing a medical laser delivery device comprising the steps of:

cutting a prismatic tip on a distal end of an optical fiber so as to direct all light in said fiber sideways to a longitudinal axis;

placing a prepared cap over said distal end of said fiber;

bonding said cap at its open end to said fiber to create a gas pocket around said prismatic fiber tip;

modifying a sector of said cap by directing a concentrated heat source at said sector and allowing it to collapse inward to form a bi-directional lens which can focus or collimate an output beam as it passes through said sector during operation of said device.

6. A method of manufacturing according to claim 5, wherein said lens is formed such that a central portion of said lens is fused to said fiber.

7. A method of manufacturing according to claim 5, wherein the step of bonding said cap to said fiber includes directing either a laser or other concentrated heating source near said open end of said cap and circumferentially fusing said cap to said fiber's surface.

8. A method of manufacturing according to claim 7, further including the step of heating said cap uniformly with a diffuse, controlled heat source to warm said gas pocket to a predetermined temperature, before said cap is circumferentially fused to said fiber's surface.

* * * * *